United States Patent
Biering et al.

(10) Patent No.: US 8,658,191 B2
(45) Date of Patent: Feb. 25, 2014

(54) DISINFECTION AGENT FOR SUCTION SYSTEMS USED IN THE FIELD OF MEDICINE OR DENTISTRY

(75) Inventors: Holger Biering, Grevenbroich (DE); Friedrich Von Rheinbaben, Monheim (DE); Michael Decker, Solingen (DE)

(73) Assignee: Ecolab USA Inc., St. Paul, MN (US)

( * ) Notice: Subject to any disclaimer, the term of this patent is extended or adjusted under 35 U.S.C. 154(b) by 901 days.

(21) Appl. No.: 11/463,436

(22) Filed: Aug. 9, 2006

(65) Prior Publication Data

US 2006/0293206 A1 Dec. 28, 2006

Related U.S. Application Data

(63) Continuation-in-part of application No. 10/499,798, filed as application No. PCT/EP02/14222 on Dec. 13, 2002, now abandoned.

(30) Foreign Application Priority Data

Dec. 22, 2001 (DE) .................................. 101 63 845

(51) Int. Cl.
*A01N 25/00* (2006.01)
(52) U.S. Cl.
USPC ........................................................ 424/405
(58) Field of Classification Search
USPC ........................................................ 424/405
See application file for complete search history.

(56) References Cited

U.S. PATENT DOCUMENTS

| 4,737,541 | A | * | 4/1988 | Stavenger et al. | 524/547 |
|---|---|---|---|---|---|
| 5,403,505 | A | * | 4/1995 | Hachmann et al. | 510/383 |
| 5,554,656 | A | | 9/1996 | Loewer | |
| 5,576,284 | A | | 11/1996 | Van Buskirk | |
| 6,331,607 | B1 | | 12/2001 | Bohlander | |
| 6,610,248 | B1 | | 8/2003 | Lichtenberg | |

FOREIGN PATENT DOCUMENTS

| DE | 4007758 | | 9/1991 |
|---|---|---|---|
| DE | 4010615 | A1 | 10/1991 |
| DE | 19603977 | | 8/1997 |
| DE | 19613881 | | 9/1997 |
| DE | 20017213 | | 12/2000 |

OTHER PUBLICATIONS

Meyer et al (Journal of Hospital Infection, vol. 42, Issue 2, Jun. 1999, pp. 151-154).*
International Search Report, dated Mar. 31, 2003 for corresponding PCT Application No. PCT/EP02/14222 (3 pages).
English-language translation of International Preliminary Examination Report, dated Mar. 23, 2004 for corresponding PCT Application No. PCT/EP02/14222 (5 pages).
English-language abstract for DE4010615 (Kaltenbach & Voight).

* cited by examiner

*Primary Examiner* — Benjamin Packard
(74) *Attorney, Agent, or Firm* — Merchant & Gould P.C.

(57) ABSTRACT

Concentrated or ready-for-use disinfecting agent for medical or dental suction apparatus and related equipment, comprising a special active ingredient of amine compounds and having a viscosity between 100 and 2000 mPas, preferably between 350 and 1000 mPas.

18 Claims, No Drawings

DISINFECTION AGENT FOR SUCTION SYSTEMS USED IN THE FIELD OF MEDICINE OR DENTISTRY

CROSS REFERENCE TO RELATED APPLICATION

This application is a continuation-in-part of U.S. patent application Ser. No. 10/499,798, filed Aug. 5, 2004, the entire disclosure of which is incorporated herein by reference in its entirety.

FIELD OF THE INVENTION

The present invention lies in the area of disinfection for a suction apparatus and related equipment in the medical and dental fields. It concerns disinfection agents for medical or dental suction apparatus as well as, as a further subject, the method for care of the corresponding apparatus and the use of a disinfecting agent of that kind for destroying bacteria and/or fungi in the corresponding suction apparatus.

BACKGROUND OF THE INVENTION

It is necessary particularly in the medical and dental sectors to take all feasible measures which not only guarantee the safety of patients by preventing possible transfer of pathogenic or facultatively pathogenic germs, but also to avoid annoyance by odiferous bacteria.

One possible incubator for germs of that kind is a suction apparatus in the medical or dental fields, which accordingly have to be regularly cleaned and disinfected. For example, with a dental suction apparatus, a mixture flow of air, water, saliva, tooth material and the like is sucked out of the patient's mouth, separated from the air and the remainder fed to an outflow. Constituents of the mixture flow deposit in the suction hoses and pipe ducts, particularly bacteria, blood residues and further contaminants. It has been attempted to satisfy the requirements of hygiene by regular rinsing or other treatment with disinfecting agent and water mixtures. For the purpose of disinfection there have in the past usually been used liquid disinfecting agent concentrate on the basis of quaternary ammonium compounds, which are diluted before use. The disadvantage of this method consists in an insufficient dwell time of the disinfecting solution in the suction apparatus, as rivulets form in the suction hose by reason of flow technology, whereby a uniform wetting of the inner surfaces of the hoses is not provided. Moreover, the quaternary ammonium compounds employed have only a limited spectrum of efficacy against bacteria, fungus and cloaked virii. In particular, efficacy relative to mycobacteria is not guaranteed with these active ingredients.

A further possibility of use of the state of the art is represented by the use of pulverulent or granulated disinfecting agents according to DE 40 10 615. If the use is carried out after previous moistening of the suction system, then a longer dwell time as well as a sufficiently uniform wetting are possible in the case of the method according to DE 40 10 615. However, the disadvantage of this method consists in guaranteeing a homogenous distribution of the disinfecting active ingredient in the product mixture used, which contains further solid recipe constituents, such as, for example, builders, cleaning components and further ingredients. The requisite homogeneity and stability of the powder mixture or granulate is achievable only by technically involved methods. A disadvantage also consists in the limitation of the selection of possible microbicidal active ingredients, since preferably solid substances, such as, for example, quaternary ammonium compounds or salts of chlorisocyanuric acid or of tosylchloramide can come into use. The disadvantages of the use of quaternary ammonium compounds were already described. On the other hand, chlorine-containing active ingredients are AOX-forming substances, the introduction of which into communal waste water systems is restricted. By AOX-forming substances there is understood, in accordance with the present invention, that these compounds can lead to formation of organic halogen compounds absorbable at active chlorine.

SUMMARY

Accordingly, the present invention has the object of making available a disinfecting agent for a suction apparatus, which guarantees a uniform distribution of the active substances in the suction apparatus and ensures a sufficient dwell time for the destruction or inactivation of a wide ranging germ spectrum, particularly mycobacteria and adenoviri.

DETAILED DESCRIPTION OF SOME EMBODIMENTS

Active Ingredients

The subject of the present invention is consequently a concentrated, ready-for-use disinfecting agent for medical or dental suction equipment, comprising an active ingredient selected from the group of alkylpropylenediamines with the general formula I

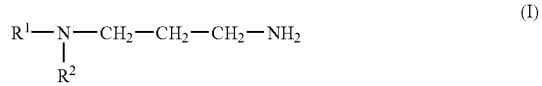

wherein $R^1$ signifies an alkyl or alkenyl group with 8 to 18 carbon atoms and $R_2$ signifies hydrogen, an alkyl group with 1 to 4 carbon atoms or an amino alkyl group with 2 to 4 carbon atoms and/or the group of products known as GLUCOPROTAMIN (Registered Trade Mark) and available in the mol ratio 1:1 to 1:2 at 60 to 175° C. from alkylpropylenediamine of the formula II

in which $R^3$ stands for a linear alkyl group with 12 to 14 carbon atoms, by conversion with compounds of the formula III

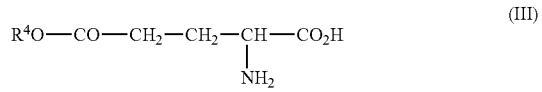

in which $R^4$ stands for hydrogen or an alkyl group with 1 to 4 carbon atoms, characterised in that the ready-for-use agent has a viscosity between 100 and 2000 mPas, preferably between 350 and 1000 mPas, measured by a Brookfield digital viscometer, model LVTDV-II, at a test temperature of 20° C. with use of spindle No. 2 (LV-series code number 62) with a spindle rotational speed of 12 revolutions per minute, wherein the value was read off after 60 seconds. In that case, ready-for-use means that the agent, which is introduced directly into the suction apparatus, has the stated properties.

The disinfecting agent can include one or more amine disinfecting agents. The disinfecting agent according to the invention preferably contains GLUCOPROTAMIN (Registered Trade Mark), N,N-bis(3-aminopropyl)-laurylamine, N-dodecyl-1,3-propanediamine, N-cocos-1,3-propanediamine or a mixture therefrom as said active ingredient.

Preferably, 0.01 to 30 weight percent, particularly 0.1 to 15 weight percent, of one or more of the said active ingredients are present in the disinfecting agent according to the invention.

Second Active Ingredient

In a further preferred form of embodiment the disinfecting agent according to the invention additionally contains a second active ingredient selected from the group of quaternary ammonium compounds of the formula I

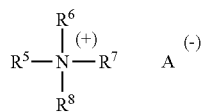

(I)

in which R5 signifies an alkyl group with 6 to 16 carbon atoms, $R^6$ signifies an alkyl group with 1 to 12 carbon atoms or a benzyl group, $R^7$ and $R^8$ signify alkyl groups with 1 to 4 carbon atoms or hydroxyalkyl groups with 2 to 4 carbon atoms and A(−) represents the equivalent amount of a corresponding anion such as an alkali metal or alkaline earth metal anion.

Particularly preferred active ingredients according to formula I are in that case benzalkonium chloride and/or dimethyl-dioctylammonium chloride.

In that case it is furthermore preferred that 0.01 to 30 weight percent, particularly 0.1 to 15 weight percent, of the said second active ingredient are present, referred to the total agent, in the disinfecting agent according to the invention.

Thickener

The advantage of the disinfecting agent according to the present invention is that after use on the inner surface of the suction hose or the pipe it forms a coherent layer, wherein this layer over a specific period of time, which is dependent on the viscosity of the disinfecting agent, does not substantially completely deliquesce. A disinfecting agent in an unthickened or water-thin liquid phase is accordingly not a composition in the sense of the present invention, since such a solution almost instantly deliquesces after introduction into the suction apparatus.

A prerequisite is also that the disinfecting agent according to the invention can be washed away again after application and action.

In principle, any thickened liquid or gel of dispersed phase and dispersing agent can serve as a basis of the preparation insofar as the components do not react in undesired manner with the active ingredient components according to the invention. Some non-limiting examples of suitable thickeners include organic and inorganic thickeners. Of the organic thickeners there are (1) cellulosic thickeners and their derivatives, (2) natural gums, (3) crosslinked acrylates and sulfonates, (4) starches, (5) stearates, and (6) fatty acid alcohols. Of the inorganic thickeners there are (7) clays, and (8) salts. Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of crosslinked acrylates and sulfonates include potassium aluminum polyacrylate, sodium acrylate/vinyl alcohol copolymer, sodium polymethacrylate, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, and the like. Some non-limiting examples of fatty acid alcohols include caprylic alcohol, cetearyl alcohol, lauryl alcohol, oleyl alcohol, palm kernel alcohol, and the like. Some non-limiting examples of clays include bentonite, magnesium aluminum silicate, magnesium trisilicate, stearalkonium bentonite, tromethamine magnesium aluminum silicate, and the like. Some non-limiting examples of salts include calcium chloride, sodium chloride, sodium sulfate, ammonium chloride, and the like.

The composition may contain one thickener or a mixture of two or more thickeners. Preferred thickeners do not adversely react with other raw materials in the composition. For example, in some embodiments, the composition may include cationic raw materials such as quaternary ammonium compounds. In those embodiments, it may be preferred to have a nonionic or cationic thickener that does not adversely react with the cationic raw materials. It is understood that a person skilled in the art will know how to select an appropriate thickener and control any adverse reactions through formulating.

The composition may contain one thickener, or more than one thickener. Preferably, gels on a water base are used, particularly gels on a water base with dispersed organic gel-forming agents. For example, gels such as those described in German laid-open specification DE-OS 38 36 138 are usable. Hydrophilic organic gels on the basis of modified fatty alcohol alkoxylate as well as synthetically produced polymers, preferably gels on the basis of polyvinylalcohol or polyacrylic acid derivative, are particularly preferred.

Preferred commercially available thickeners are the raw materials 'Optiflo' (Registered Trade Mark) H 600/E of the company Süd-Chemie and PLURIOL A 5000 T 85 of the company BASF. 'Optiflo' H 600/E is a non-ionic, hydrophobic modified polymer and PLURIOL A 5000 T 85 is a modified fatty alcohol oxylate.

However, other thickeners, such as carboxymethylcellulose and non-ionically and cationically modified polyacrylates, also come into question.

Additional Functional Ingredients

The preparation can contain further usual additives, such as dyes and fragrances, antifoaming agents, corrosion inhibitors, sequesterants or chelating agents, additional surfactants, diluting agents, enzymes, preservatives, oxidation (bleaching) agents, and mixtures thereof.

Dyes and Fragrances

The composition may optionally include a dye. Examples of dyes include any water soluble or product soluble dye, any FD&C or D&C approved dye, Blue 1, FD&C Yellow 5, Resorcin Brown, Red 40, Direct Blue 86 (Miles), Basic Violet 10 (Clariant), Acid Yellow 23 (GAF), Acid Yellow 17 (Sigma Chemical), Sap Green (Keyston Analine and Chemical), Metanil Yellow (Keyston Analine and Chemical), Acid Blue 9 (Hilton Davis), Sandolan Blue/Acid Blue 182 (Clariant), Hisol Fast Red (Capitol Color and Chemical), Fluorescein (Capitol Color and Chemical), Acid Green 25 (Ciba Specialties), and the like. The dye is preferably a water soluble dye. Also, the dye is preferably a FD&C or D&C approved dye.

The composition may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals.

Antifoaming Agents

The composition may optionally include an antifoaming agent, also referred to as a defoaming agent or foam inhibitor. A defoaming agent or foam inhibitor may be included for reducing the stability of any foam that is formed. Examples of foam inhibitors include silicon compounds such as silica dispersed in polydimethylsiloxane, fatty amides, hydrocarbon waxes, fatty acids, fatty esters, fatty alcohols, fatty acid soaps, ethoxylates, mineral oils, polyethylene glycol esters, polyoxyethylene-polyoxypropylene block copolymers, alkyl phosphate esters such as monostearyl phosphate and the like. A discussion of foam inhibitors may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated by reference herein.

Corrosion Inhibitors

The composition may optionally include a corrosion inhibitor. Corrosion inhibitors provide compositions that generate surfaces that are less prone to biofilm buildup. Preferred corrosion inhibitors which can be used according to the invention include phosphonates, phosphonic acids, triazoles, organic amines, sorbitan esters, carboxylic acid derivatives, sarcosinates, phosphate esters, zinc, nitrates, chromium, molybdate containing components, and borate containing components. Exemplary phosphates or phosphonic acids are available under the name Dequest (i.e., Dequest 2000, Dequest 2006, Dequest 2010, Dequest 2016, Dequest 2054, Dequest 2060, and Dequest 2066) from Solutia, Inc. of St. Louis, Mo. Exemplary triazoles are available under the name Cobratec (i.e., Cobratec 100, Cobratec TT-50-S, and Cobratec 99) from PMC Specialties Group, Inc. of Cincinnati, Ohio. Exemplary organic amines include aliphatic amines, aromatic amines, monoamines, diamines, triamines, polyamines, and their salts. Exemplary amines are available under the names Amp (i.e. Amp-95) from Angus Chemical Company of Buffalo Grove, Ill.; WGS (i.e., WGS-50) from Jacam Chemicals, LLC of Sterling, Kans.; Duomeen (i.e., Duomeen O and Duomeen C) from Akzo Nobel Chemicals, Inc. of Chicago, Ill.; DeThox amine (C Series and T Series) from DeForest Enterprises, Inc. of Boca Raton, Fla.; Deriphat series from Henkel Corp. of Ambler, Pa.; and Maxhib (AC Series) from Chemax, Inc. of Greenville, S.C. Exemplary sorbitan esters are available under the name Calgene (LA-series) from Calgene Chemical Inc. of Skokie, Ill. Exemplary carboxylic acid derivatives are available under the name Recor (i.e., Recor 12) from Ciba-Geigy Corp. of Tarrytown, N.Y. Exemplary sarcosinates are available under the names Hamposyl from Hampshire Chemical Corp. of Lexington, Mass.; and Sarkosyl from Ciba-Geigy Corp. of Tarrytown, N.Y.

Sequestrants or Chelating Agents

The composition may optionally include a chelating agent, sequestering agent, or builder. These ingredients generally provide cleaning properties and chelating properties. Exemplary detergent builders that may be used include sodium sulphate, sodium chloride, starch, sugars, $C_1$-$C_{10}$ alkylene glycols such as propylene glycol, and the like. Exemplary chelating agents that may be used include phosphates, phosphonates, carboxylates, and amino-acetates. Exemplary phosphates that may be used include sodium orthophosphate, potassium orthophosphate, sodium pyrophosphate, potassium pyrophosphate, sodium tripolyphosphate (STPP), and sodium hexametaphosphate. Exemplary phosphonates that may be used include 1-hydroxyethane-1,1-diphosphonic acid, aminotrimethylene phosphonic acid, diethylenetriaminepenta(methylenephosphonic acid), 1-hydroxyethane-1,1-diphosphonic acid $CH_3C(OH)[PO(OH)_2]_2$, aminotri(methylenephosphonic acid) $N[CH_2PO(OH)_2]_3$, aminotri(methylenephosphonate), sodium salt

2-hydroxyethyliminobis(methylenephosphonic acid) $HOCH_2CH_2N[CH_2PO(OH)_2]_2$, diethylenetriaminepenta(methylenephosphonic acid) $(HO)_2POCH_2N[CH_2CH_2N[CH_2PO(OH)_2]_2]_2$, diethylenetriaminepenta(methylenephosphonate), sodium salt $C_9H_{(28-x)}N_3Na_xO_{15}P_5$ (x=7), hexamethylenediamine(tetramethylenephosphonate), potassium salt $C_{10}H_{(28-x)}N_2K_xO_{12}P_4$ (x=6), bis(hexamethylene) triamine(pentamethylenephosphonic acid) $(HO_2)POCH_2N[(CH_2)_6N[CH_2PO(OH)_2]_2]_2$, and phosphorus acid $H_3PO_3$. Exemplary amino-acetates include aminocarboxylic acids such as N-hydroxyethyliminodiacetic acid, nitrilotriacetic acid (NTA), ethylenediaminetetraacetic acid (EDTA), N-hydroxyethyl-ethylenediaminetriacetic acid (HEDTA), and diethylenetriaminepentaacetic acid (DTPA). Exemplary carboxylates that may be used include tartaric acid, glucoheptonic acid, glycolic acid, 2-hydroxyacetic acid; 2-hydroxypropanoic acid; 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxypropanoic acid; 2,3-dihydroxypropanoic acid; 2,3,4-trihydroxybutanoic acid; 2,3,4,5-tetrahydroxypentanoic acid; 2,3,4,5,6-pentahydroxyhexanoic acid; 2-hydroxydodecanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy-4-methylpentanoic acid; 3-hydroxy-4-methoxymandelic acid; 4-hydroxy-3-methoxymandelic acid; 2-hydroxy-2-methylbutanoic acid; 3-(2-hydroxyphenyl)lactic acid; 3-(4-hydroxyphenyl)lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutaned-ioic acid; citric acid; isocitric acid; agaricic acid; quinic acid; glucuronic acid; glucuronolactone; galacturonic acid; galacturonolactone; uronic acids; uronolactones; dihydroascorbic acid; dihydroxytartaric acid; tropic acid; ribonolactone; gluconolactone; galactonolactone; gulonolactone; mannonolactone; ribonic acid; gluconic acid; citramalic acid; pyruvic acid; hydroxypyruvic acid; hydroxypyruvic acid phosphate; methylpyruvate; ethyl pyruvate; propyl pyruvate; isopropyl pyruvate; phenyl pyruvic acid; methyl phenyl pyruvate; ethyl phenyl pyruvate; propyl phenyl pyruvate; formyl formic acid; methyl formyl formate; ethyl formyl formate; propyl formyl formate; benzoyl formic acid; methyl benzoyl formate; ethyl benzoyl formate;

propyl benzoyl formate; 4-hydroxybenzoyl formic acid; 4-hydroxyphenyl pyruvic acid; 2-hydroxyphenyl pyruvic acid.

Surfactants

The composition may optionally include a surfactant such as an anionic surfactant, cationic surfactant, nonionic surfactant, and amphoteric surfactant. Examples of these surfactants are well known in the art.

Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants in the present invention include:

1. Block polyoxypropylene-polyoxyethylene polymeric compounds based upon propylene glycol, ethylene glycol, glycerol, trimethylolpropane, and ethylenediamine as the initiator reactive hydrogen compound. Examples of polymeric compounds made from a sequential propoxylation and ethoxylation of initiator are commercially available under the trade names Pluronic® and Tetronic® manufactured by BASF Corp.

Pluronic® compounds are difunctional (two reactive hydrogens) compounds formed by condensing ethylene oxide with a hydrophobic base formed by the addition of propylene oxide to the two hydroxyl groups of propylene glycol. This hydrophobic portion of the molecule weighs from 1,000 to 4,000. Ethylene oxide is then added to sandwich this hydrophobe between hydrophilic groups, controlled by length to constitute from about 10% by weight to about 80% by weight of the final molecule.

Tetronic® compounds are tetra-functional block copolymers derived from the sequential addition of propylene oxide and ethylene oxide to ethylenediamine. The molecular weight of the propylene oxide hydrotype ranges from 500 to 7,000; and, the hydrophile, ethylene oxide, is added to constitute from 10% by weight to 80% by weight of the molecule.

2. Condensation products of one mole of alkyl phenol wherein the alkyl chain, of straight chain or branched chain configuration, or of single or dual alkyl constituent, contains from 8 to 18 carbon atoms with from 3 to 50 moles of ethylene oxide. The alkyl group can, for example, be represented by diisobutylene, di-amyl, polymerized propylene, iso-octyl, nonyl, and di-nonyl. These surfactants can be polyethylene, polypropylene, and polybutylene oxide condensates of alkyl phenols. Examples of commercial compounds of this chemistry are available on the market under the trade names Igepal® manufactured by Rhone-Poulenc and Triton® manufactured by Union Carbide.

3. Condensation products of one mole of a saturated or unsaturated, straight or branched chain alcohol having from 6 to 24 carbon atoms with from 3 to 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol® manufactured by Shell Chemical Co. and Alfonic® manufactured by Vista Chemical Co.

4. Condensation products of one mole of saturated or unsaturated, straight or branched chain carboxylic acid having from 8 to 18 carbon atoms with from 6 to 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol® manufactured by Henkel Corporation and Lipopeg® manufactured by Lipo Chemicals, Inc.

In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention. All of these ester moieties have one or more reactive hydrogen sites on their molecule which can undergo further acylation or ethylene oxide (alkoxide) addition to control the hydrophilicity of these substances.

Examples of nonionic low foaming surfactants include:

5. Compounds from (1) which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from 1,000 to 3,100 with the central hydrophile including 10% by weight to 80% by weight of the final molecule. These reverse Pluronics® are manufactured by BASF Corporation under the trade name Pluronic® R surfactants.

Likewise, the Tetronic® R surfactants are produced by BASF Corporation by the sequential addition of ethylene oxide and propylene oxide to ethylenediamine. The hydrophobic portion of the molecule weighs from 2,100 to 6,700 with the central hydrophile including 10% by weight to 80% by weight of the final molecule.

6. Compounds from groups (1), (2), (3) and (4) which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

7. The alkylphenoxypolyethoxyalkanols of U.S. Pat. No. 2,903,486 issued Sep. 8, 1959 to Brown et al. and represented by the formula

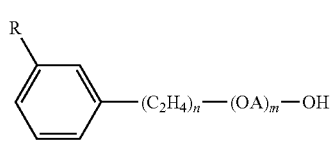

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n(C_2H_4O)_mH$ wherein Y is the residue of organic compound having from 1 to 6 carbon atoms and one reactive hydrogen atom, n has an average value of at least 6.4, as determined by hydroxyl number and m has a value such that the oxyethylene portion constitutes 10% to 90% by weight of the molecule.

The conjugated polyoxyalkylene compounds described in U.S. Pat. No. 2,674,619, issued Apr. 6, 1954 to Lundsted et al. having the formula $Y[(C_3H_6O)_n(C_2H_4O)_mH]_x$ wherein Y is the residue of an organic compound having from 2 to 6 carbon atoms and containing x reactive hydrogen atoms in which x has a value of at least 2, n has a value such that the molecular weight of the polyoxypropylene hydrophobic base is at least 900 and m has value such that the oxyethylene content of the molecule is from 10% to 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n(C_2H_4O)_mH]_x$ wherein P is the residue of an organic compound having from 8 to 18 carbon atoms and containing x reactive hydrogen atoms in which x has a value of 1 or 2, n has a value such that the molecular weight of the polyoxyethylene portion is at least 44 and m has a value such that the oxypropylene content of the molecule is from 10% to 90% by weight. In either case the oxypropylene chains may contain optionally, but advantageously, small amounts of ethylene oxide and the oxyethylene chains may contain also optionally, but advantageously, small amounts of propylene oxide.

8. Polyhydroxy fatty acid amide surfactants suitable for use in the present compositions include those having the structural formula $R^2CONR^1Z$ in which: $R^1$ is H, $C_1$-$C_4$ hydrocarbyl, 2-hydroxy ethyl, 2-hydroxy propyl, ethoxy, propoxy group, or a mixture thereof, $R^2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glycityl moiety.

9. The alkyl ethoxylate condensation products of aliphatic alcohols with from 0 to 25 moles of ethylene oxide are suitable for use in the present compositions. The alkyl chain of the aliphatic alcohol can either be straight or branched, primary or secondary, and generally contains from 6 to 22 carbon atoms.

10. The ethoxylated $C_6$-$C_{18}$ fatty alcohols and $C_6$-$C_{18}$ mixed ethoxylated and propoxylated fatty alcohols are suitable surfactants for use in the present compositions, particularly those that are water soluble. Suitable ethoxylated fatty alcohols include the $C_{10}$-$C_{18}$ ethoxylated fatty alcohols with a degree of ethoxylation of from 3 to 50.

11. Suitable nonionic alkylpolysaccharide surfactants include those disclosed in U.S. Pat. No. 4,565,647, Llenado, issued Jan. 21, 1986. These surfactants include a hydrophobic group containing from 6 to 30 carbon atoms and a polysaccharide, e.g., a polyglycoside, hydrophilic group containing from 1.3 to 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

12. Fatty acid amide surfactants suitable for use in the present compositions include those having the formula: $R^6CON(R^7)_2$ in which $R^6$ is an alkyl group containing from 7 to 21 carbon atoms and each $R^7$ is independently hydrogen, $C_1$-$C_4$ alkyl, $C_1$-$C_4$ hydroxyalkyl, or $—(C_2H_4O)_xH$, where x is in the range of from 1 to 3.

13. A useful class of non-ionic surfactants includes the class defined as alkoxylated amines or, most particularly, alcohol alkoxylated/aminated/alkoxylated surfactants. These non-ionic surfactants may be at least in part represented by the general formulae:

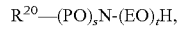

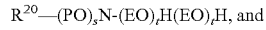

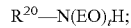

in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula:

in which $R^{20}$ is as defined above, v is 1 to 20 (e.g., 1, 2, 3, or 4 (preferably 2)), and w and z are independently 1-10, preferably 2-5.

These compounds are represented commercially by a line of products sold by Huntsman Chemicals as nonionic surfactants. A preferred chemical of this class includes Surfonic™ PEA 25 Amine Alkoxylate.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Semi-Polar Nonionic Surfactants

The semi-polar type of nonionic surface active agents are another class of nonionic surfactants The semi-polar nonionic surfactants include the amine oxides, phosphine oxides, sulfoxides and their alkoxylated derivatives.

14. Amine oxides are tertiary amine oxides corresponding to the general formula:

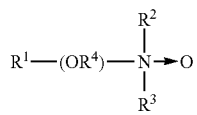

wherein the arrow is a conventional representation of a semi-polar bond; and $R^1$, $R^2$, and $R^3$ may be aliphatic, aromatic, heterocyclic, alicyclic, or combinations thereof Generally, for amine oxides of detergent interest, $R^1$ is an alkyl radical of from 8 to 24 carbon atoms; $R^2$ and $R^3$ are alkyl or hydroxyalkyl of 1-3 carbon atoms or a mixture thereof, $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to 20.

Useful water soluble amine oxide surfactants are selected from the coconut or tallow alkyl di-(lower alkyl)amine oxides, specific examples of which are dodecyldimethylamine oxide, tridecyldimethylamine oxide, tetradecyldimethylamine oxide, pentadecyldimethylamine oxide, hexadecyldimethylamine oxide, heptadecyldimethylamine oxide, octadecyldimethylamine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

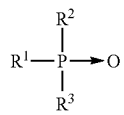

wherein the arrow is a conventional representation of a semi-polar bond; and $R^1$ is an alkyl, alkenyl or hydroxyalkyl moiety ranging from 10 to 24 carbon atoms in chain length; and $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphine oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

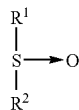

wherein the arrow is a conventional representation of a semi-polar bond; and, $R^1$ is an alkyl or hydroxyalkyl moiety of 8 to 28 carbon atoms, from 0 to 5 ether linkages and from 0 to 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

If anionic surfactants are used, then due to the foaming behaviour and the compatibility with cationic active ingredients and/or GLUCOPROTAMIN they are used only in such small quantities.

Enzymes

The composition may optionally include an enzyme. Some non-limiting examples of enzymes include a protease, an amylase, a lipase, a gluconase, a cellulase, a peroxidase, or a mixture thereof of any suitable origin, such as vegetable, animal, bacterial, fungal or yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases.

A valuable reference on enzymes is "Industrial Enzymes," Scott, D., in *Kirk-Othmer Encyclopedia of Chemical Technology*, 3rd Edition, (editors Grayson, M. and EcKroth, D.) Vol. 9, pp. 173-224, John Wiley & Sons, New York, 1980.

Preservatives

The composition may optionally include a preservative. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds and miscellaneous compounds. Some non-limiting examples of phenolic antimicrobial agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof Some non-limiting examples of halogen compounds include trichlorohydroxy diphenyl ether (Triclosan), sodium trichloroisocyanurate, sodium dichloroisocyanurate, iodine-poly(vinylpyrolidin-onen) complexes, and bromine compounds such as 2-bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of metal derivatives include silver borosilicate, silver magnesium aluminum phosphate, copper usnate, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate.

Oxidation (Bleaching) Agents

The composition may optionally include an oxidation or bleaching agent. Some non-limiting examples of suitable oxidation or bleaching agents include bleaching compounds capable of liberating an active halogen species, such as $Cl_2$, $Br_2$, —$OCl^-$ and/or —$OBr^-$. Suitable bleaching agents include, for example, chlorine-containing compounds such as a chlorine, a hypochlorite, chloramine. Preferred halogen-releasing compounds include the alkali metal dichloroisocyanurates, chlorinated trisodium phosphate, the alkali metal hypochlorites, monochlorarrine and dichloramine, and the like. Encapsulated bleaching sources may also be used to enhance the stability of the bleaching source in the composition (see, for example, U.S. Pat. Nos. 4,618,914 and 4,830, 773, the disclosure of which is incorporated by reference herein). A bleaching agent may also be a peroxygen or active oxygen source such as hydrogen peroxide, perborates, sodium carbonate peroxyhydrate, phosphate peroxyhydrates, potassium permonosulfate, and sodium perborate mono and tetrahydrate, with and without activators such as tetraacetyl-ethylene diamine, and the like.

Composition and Methods of Use

The composition can be a concentrate or a ready-to-use composition. The concentrate refers to the composition that is diluted to form the ready-to-use composition. The ready-to-use composition refers to the composition that is applied to the medical or dental suction apparatus or related equipment. The ready-for-use disinfecting composition according to the invention preferably lies at a pH value of 8 to 12, particularly preferably 9 to 11.

The composition is preferably a water-based composition where the raw materials described above are carried or diluted with water.

The composition can be used as part of a method for the care of a medical or dental suction apparatus and related equipment, particularly of the suction hose thereof, in which a disinfecting agent according to the invention is introduced in the suction region. The disinfecting agent may be introduced by applying the agent to the apparatus or equipment, inserting the agent into the apparatus or equipment, sucking the agent into the apparatus or equipment or otherwise bringing the agent into contact with the apparatus or equipment. When treating the suction hose of a medical or dental suction apparatus, the composition of the invention is preferably applied to the hose by sucking the concentrate or the use solution into the suction hose. Upon suction, the thickened composition will form a substantially even layer along the inside of the suction hose, allowing the composition to disinfect the inside of the suction hose. Thereafter, the composition will be allowed to remain on the inside of the suction hose for a period of time. For example, the composition may be allowed to remain on the inside of the suction hose for at least about 1 minute, 5 minutes, 10 minutes, 30 minutes, 60 minutes, or 90 minutes. After remaining on the inside of the suction hose for a period of time, the composition will be rinsed from the suction hose by sucking water into the suction hose for a period of time sufficient to rinse the thickened disinfectant composition away.

When treating equipment related to the suction apparatus such as a spittoon, collection tank, pipe, duct, or other equipment, the composition of the invention may applied to the equipment manually (i.e., by pouring the composition onto or into the piece of equipment), or otherwise applying, contacting, or inserting the composition into the equipment, or via the suction hose if the equipment is attached to the suction hose and part of the flow path through the suction hose. As with the suction hose, the composition may be allowed to remain on the equipment for a period of time. For example, the composition may be allowed to remain on the equipment for at least about 1 minute, 5 minutes, 10 minutes, 30 minutes, 60 minutes, or 90 minutes. Thereafter, the composition will be rinsed from the equipment by pouring, applying, or contacting water onto or into the equipment or by sucking water into the suction hose for a period of time sufficient to rinse the thickened disinfectant composition away.

Moreover, the subject of the present invention is the use of a disinfecting agent according to the invention for the destruction of bacteria, particularly mycobacteria and/or fungi in medical or dental suction apparatus, particularly in the suction hose thereof as well as in the spittoon.

The following examples shall further explain the invention, without restricting it in the scope thereof.

EXAMPLES

Example 1

Production of a Disinfecting Gel According to the Invention a) 18 g of carboxymethylcellulose were dispersed in 950 g of water, combined with 1.0 g of a 50 weight percent potassium hydroxide solution and mixed under stirring.

b) After conclusion of the process of swelling of the carboxymethylcellulose (2 h to 5 h), 8 g of a 50 weight percent GLUCOPROTAMIN (Registered Trade Mark) solution, 5 g of a 70 weight percent solution of dicoctyl-dimethylammonium chloride in a water/isopropanol mixture in the ratio 2:3 and 5 g of a $C_{12-18}$-fatty-alcohol-EO-BuO adduct with 8 EO and 8 BuO were added to the solution produced under a) and intensively mixed.

Example 2

Use of the Gel Produced in Example 1.

Stainless steel bacteria supports according to DIN 10510 were contaminated with the test organism of enterococcus faecium in broth with an additional organic loading by 1% mucin and 20% of blood and dried for 2 h at room temperature. These bacteria supports were mounted in the spray mist hose of a dental suction apparatus and, in particular, a respective bacteria support at each of the beginning and the end of the hose. For the disinfecting, the hose was moistened by suction of 200 ml water; thereafter 15 ml of a gel according to Example 1, then a further 100 ml of water and thereafter once again 15 ml of a gel according to Example 1 were sucked in.

After 60 minutes of reaction time, rinsing out of the gel was carried out by suction of 500 ml of water.

The bacteria supports were subsequently removed from the hose, each extracted in 10 ml of broth and the colony count of this broth was ascertained by coating on agar plates.

In corresponding comparative tests there was used, instead of the gel according to the invention, a) an aqueous solution with like concentration of like antimicrobial active ingredients, b) but without the property of the thickening consistency, in like quantities referred to the concentration of the antimicrobial active ingredient.

The difference of the logarithms (base 10) of the ascertained colony counts were determined as the result (logarithmic reduction factor, log-Rf). The results are summarised in the following table:

| Disinfecting Agent | log-Rf |
| --- | --- |
| gel according to Example 1 | >5.2 |
| aqueous solution according to Example 1 without carboxymethylcellulose | 3.4 |
| water | 2.5 |

What is claimed is:

1. A method of disinfecting a medical or dental suction hose comprising:
   a) sucking a thickened, ready-to-use disinfectant composition into an interior suction region of the medical or dental suction hose so as to form a substantially even layer along an inside of the suction hose, the composition having a pH value of from 9 to 12, the composition comprising:
   (i) an active substance having the formula

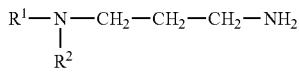

wherein $R^1$ represents an alkyl or alkenyl group with 8 to 18 carbon atoms and $R^2$ is selected from the group consisting of hydrogen, an alkyl group with 1 to 4 carbon atoms, an amino alkyl group with 2 to 4 carbon atoms, and Glucoprotamin; and
      (ii) a cellulosic thickener present in an amount sufficient to provide a viscosity between 350 and 1000 mPas when measured by a Brookfield digital viscometer at 20° C. using spindle no. 2 at a rotation of 12 revolutions per minute;
   b) allowing the composition to stay in the interior suction region of the suction hose a period of time, wherein the pH of the composition during this period of time remains from 9 to 12; and
   c) rinsing the suction hose with water.

2. The method of claim 1, wherein the active substance is selected from the group consisting of Glucoprotamin, N,N-bis(3-aminopropyl)laurylamine, N-dodecyl-1,3-propanediamine, N-coco-1,3-propanediamine, and mixtures thereof.

3. The method of claim 1, wherein the active substance is present from about 0.01 to about 30 wt. %.

4. The method of claim 1, wherein the active substance is present from about 0.01 to about 15 wt. %.

5. The method of claim 1, the composition further comprising a second active substance comprising a quaternary ammonium compound having the formula

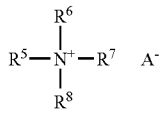

wherein $R^5$ represents an alkyl group with 6 to 16 carbon atoms, $R^6$ is selected from the group consisting of a alkyl group with 1 to 12 carbon atoms, and a benzyl group, and $R^7$ and $R^8$ are selected from the group consisting of an alkyl group with 1 to 4 carbon atoms and a hydroxyl alkyl group with 2 to 4 carbon atoms, and $A^-$ represents a charge compensating anion.

6. The method of claim 5, wherein the second active substance is selected from the group consisting of benzalkonium chloride and dimethyldioctylammonium chloride.

7. The method of claim 5, wherein the second active substance is present from about 0.01 to about 30 wt. %.

8. The method of claim 5, wherein the second active substance is present from about 0.1 to about 15 wt. %.

9. The method of claim 1, wherein the composition has a pH from 9 to 11.

10. The method of claim 1, the composition further comprising a component selected from the group consisting of dyes, fragrances, anti foaming agents, corrosion inhibitors, sequesterants or chelating agents, additional surfactants, diluting agents, enzymes, preservatives, oxidation agents, and mixtures thereof.

11. The method of claim 1, wherein the composition is effective at destroying a microorganism selected from the group consisting of a bacteria, a fungus, and mixtures thereof.

12. The method of claim 1, wherein the composition is effective at destroying mycobacteria.

13. The method of claim 1, wherein the composition is allowed to stay in the interior suction region of the suction hose for at least about 1 minute.

14. The method of claim 1, wherein the composition is allowed to stay in the interior suction region of the suction hose for at least about 60 minutes.

15. The method of claim 1, wherein the composition is allowed to stay in the interior suction region of the suction hose for at least about 5 minutes.

16. A method of disinfecting a medical or dental suction apparatus comprising:
   sucking a thickened, ready-to-use disinfectant composition into the medical or dental suction apparatus, the composition having a pH value of from 9 to 12 and a viscosity of between about 350 and 1000 mPas, the composition comprising:
   (i) an active substance having the formula

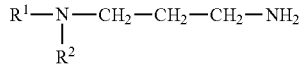

wherein $R^1$ represents an alkyl or alkenyl group with 8 to 18 carbon atoms and $R^2$ is selected from the group consisting of hydrogen, an alkyl group with 1 to 4 carbon atoms, an amino alkyl group with 2 to 4 carbon atoms, and Glucoprotamin; and
   (ii) a thickener;
   b) allowing the composition to stay in the suction apparatus for at least about 5 minutes; and
   c) rinsing the suction apparatus with water.

17. The method of claim 16, wherein the composition is allowed to stay in the suction apparatus for at least about 30 minutes.

18. The method of claim 16, wherein the suction apparatus is a suction hose having an interior suction region, and said introducing step comprises introducing the composition into the interior suction region so as to form a substantially even layer along an inside of the suction hose.

* * * * *